(12) United States Patent
Van Antwerp et al.

(10) Patent No.: US 8,034,764 B2
(45) Date of Patent: Oct. 11, 2011

(54) MODULATION OF SOCS EXPRESSION IN THERAPEUTIC REGIMENS

(75) Inventors: William P. Van Antwerp, Valencia, CA (US); Poonam S. Gulati, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/936,390

(22) Filed: Sep. 8, 2004

(65) Prior Publication Data

US 2005/0084477 A1 Apr. 21, 2005

Related U.S. Application Data

(60) Provisional application No. 60/513,100, filed on Oct. 21, 2003.

(51) Int. Cl.
*A61K 38/00* (2006.01)
*C07H 21/04* (2006.01)

(52) U.S. Cl. .......................................... 514/2; 536/23.1

(58) Field of Classification Search .................. None
See application file for complete search history.

(56) References Cited

U.S. PATENT DOCUMENTS

| | | | |
|---|---|---|---|
| 6,041,788 A * | 3/2000 | Shen | |
| 6,461,605 B1 * | 10/2002 | Cutler et al. | |
| 6,575,169 B2 * | 6/2003 | McMichael | |
| 2003/0191058 A1 | 10/2003 | Nicholson et al. | |

FOREIGN PATENT DOCUMENTS

| WO | WO 97/44057 | 11/1997 |
|---|---|---|
| WO | WO 2004/078127 A2 * | 9/2004 |
| WO | WO 2004/078193 A1 * | 9/2004 |
| WO | WO 2004/078194 A1 * | 9/2004 |
| WO | WO 2004/078207 A1 * | 9/2004 |

OTHER PUBLICATIONS

Hebenstreit et al., Journal of Immunology 171: 5901-5907 (Sep. 2003), "IL-4 and IL-13 induce SOCS-1 gene expression in A549 cells by three functional STAT6-binding motifs located upstream of the transcription intiation site".*
W.S. Alexander et al., "Suppressors of cytokine signaling (SOCS): negative regulators of signal transduction," 1999, J. Leukocyte Biology, 66(4):588-592.*
J.G. Bode et al., "IFN-α antagonistic activity of HCV core protein involves induction of suppressor of cytokine signaling-3[1]," Mar. 2003, The FASEB Journal, 17:488-490.*
J. Chen et al., "Stat5 is a physiological substrate of the insulin receptor," Mar. 1997, Proc. Natl. Acad. Sci. USA, 94:2295-2300.*
X.P. Chen et al., "SOCS proteins, regulators of intracellular signaling," Sep. 2000, Immunity, 13(3):287-290.*
M.M.W. Chong et al, "γ-Interferon Signaling in Pancreatic β-Cells Is Persistent but Can Be Terminated by Overexpression of Suppressor of Cytokine Signaling-1," Dec. 2001, Diabetes, 50:2744-2751.*
A.L. Cornish et al., "Suppressor of Cytokine Signaling-1 Has IFN-γ-Independent Actions in T Cell Homeostasis[1]," 2003, The Journal of Immunology, 170:878-886.*
S. Cottet et al., "SOCS-1 Protein Prevents Janus Kinase/STAT-dependent Inhibition of β Cell Insulin Gene Transcription and Secretion in Response to Interferon-γ," Jul. 13, 2001, J. Bio Chem, 276(28): 25862-25870.*
A. Crespo et al., "Low responsiveness to IFN-γ, after pretreatment of mouse macrophages with lipopolysaccharides, develops via diverse regulatory pathways," 2002, Eur. J. Immunol, 32:710-719.*
H.L. Dickensheets et al., "Interferons inhibit activation of STAT6 by interleukin 4 in human monocytes by inducing *SOCS-1* gene expression," Sep. 1999, Proc. Natl. Acad. Sci. USA, 96:10800-10805.*
B. Emanuelli et al., "SOCS-3 is an insulin-induced negative regulator of insulin signaling," May 2000, J Biol Chem., 275(21):15985-15991.*
B. Emanuelli et al., "SOCS-3 inhibits insulin signaling and is up-regulated in response to tumor necrosis factor-alpha in the adipose tissue of obese mice," Dec. 2001, J Biol Chem., 276(51):47944-47949.*
M. Federici et al., "Impaired IFN-γ-Dependent Inflammatory Responses in Human Keratinocytes Overexpressing the Suppressor of Cytokine Signaling 1[1]," 2002, The Journal of Immunology,. 168:434-442.
K. Friederichs et al., "Interleukin-6-induced proliferation of pre-B cells mediated by receptor complexes lacking the SHP2/SOCS3 recruitment sites revisited," Dec. 2001, Eur J Biochem., 268(24):6401-6407.
M. Fujimoto et al., "A regulatory role for suppressor of cytokine signaling-1 in $T_h$, polarization in vivo," 2002, International Immunology, 14(11):1343-1350.
M. Gadina et al., "Signaling by type I and II cytokine receptors: ten years after," Jun. 2001, Curr Opin Immunol., 13(3):363-373.
X. Hu et al., "Sensitization of IFN-γ Jak-STAT signaling during macrophage activation," Sep. 2002, Nature Immunology, 3(9):859-866.

(Continued)

Primary Examiner — Anand Desai
(74) Attorney, Agent, or Firm — Gates & Cooper LLP

(57) ABSTRACT

A method is provided for treating conditions that are susceptible of treatment with a cytokine wherein certain physiological processes normally associated with cytokine administration (e.g. the induction of SOCS 1 and/or SOCS 3) are diminished or eliminated. The method comprises continuously administering a controlled dose of a cytokine to an individual afflicted with a condition susceptible of treatment with the cytokine.

5 Claims, 1 Drawing Sheet

OTHER PUBLICATIONS

Y. Kawazoe et al., "Signal transducer and activator of transcription (STAT)-induced STAT inhibitor 1 (SSI-1)/suppressor of cytokine signaling 1 (SOCS1) inhibits insulin signal transduction pathway through modulating insulin receptor substrate 1 (TRS-1) phosphorylation," Jan. 2001, J Exp Med. 193(2):263-269.

M.N. Le et al., "Dual mechanism of signal transducer and activator of transcription 5 activation by the insulin receptor," Dec. 2002, Mol Endocrinol.,16(12):2764-2779.

J.A. Losman et al., "Cutting edge: SOCS-1 is a potent inhibitor of IL-4 signal transduction," Apr. 1999, J Immunol., 162(7):3770-3774.

R.A. Mooney et al., "Suppressors of cytokine signaling-1 and -6 associate with and inhibit the insulin receptor. A potential mechanism for cytokine-mediated insulin resistance," Jul. 2001, J Biol Chem., 276(28):25889-25893.

Y. Morita et al., "Signals transducers and activators of transcription (STAT)-induced STAT inhibitor-1 (SSI-1)/suppressor of cytokine signaling-1 (SOCS-1) suppresses tumor necrosis factor alpha-induced cell death in fibroblasts," May 2000, Proc Natl Acad Sci U S A., 97(10):5405-5410.

N. A. Nicola, "The suppressors of cytokine signaling (SOCS): proteins: Important feedback inhibitors of cytokine action," 2000, Experimental Hematology, 28:1105-1112.

G.M. O'Keefe et al., "IFN-$\gamma$ Regulation of Class II Transactivator Promoter IV in Macrophages and Microglia: Involvement of the Suppressors of Cytokine Signaling-1 Protein," 2001, The Journal of Immunology, 166:2260-2269.

P. Peraldi et al., "Insulin induces suppressor of cytokine signaling-3 tyrosine phosphorylation through janus-activated kinase.," Jul. 2001, J. Biol. Chem., 276(27):24614-24620.

S.G. Ronn et al., "The effect of suppressor of cytokine signaling 3 on GH signaling in beta-cells," Sep. 2002, Mol Endocrinol., 16(9):2124-2134.

C.L Sadowski et al., "Insulin Induction of SOCS-2 and SOCS-3 mRNA expression in C2C12 Skeletal Muscle Cells Is Mediated by Stat5,"Jun. 2001, J Biol Chem., 276(23):20703-20710.

H. Sakamoto et al., "A *Janus* Kinase Inhibitor, JAB, Is an Interferon-$\gamma$-Inducible Gene and Confers Resistance to Interferons," 1998, Blood, 92(5):1668-1676.

J.W. Slaton et al., "Interferon-$\alpha$-mediated Down-Regulation of Angiogenesis-related Genes and Therapy of Bladder Cancer Are Dependent on Optimization of Biological Dose and Schedule[1]," Oct. 1999, Clinical Cancer Research, 5:2726-2734.

M.M. Song et al., "The Suppressor of Cytokine Signaling (SOCS) 1 and SOCS3 but Not SOCS2 Proteins Inhibit Inteferon-mediated Antiviral and Antiproliferative Activities," Dec. 1998, J. Biol Chem., 273(52):35056-35062.

B. Sporri et al., "JAB/SOCS1/SSI-1 is an interleukin-2-induced inhibitor of IL-2 signaling," Jan. 2001, Blood, 97(1):221-226.

G.R. Stark et al., "How cells respond to interferons,"1998, Annu Rev Biochem., 67:227-264.

R. Starr et al., "A family of cytokine-inducible inhibitors of signalling," Jun. 1997, Nature, 387(6636):917-921.

S. Trop et al., "Overexpression of suppressor of cytokine signaling-1 impairs pre-T-cell receptor-induced proliferation but not differentiation of immature thymocytes," Apr. 2001, Blood, 97(8):2269-2277.

D.R. Wesemann et al., "Suppressor of Cytokine Signaling 1 Inhibits Cytokine Induction of CD40 Expression in Macrophages[1]," 2002, The Journal of Immunology, 169:2354-2360.

H. Yasukawa et al., "Negative Regulation of Cytokine Signaling Pathways," 2000, Annu. Rev. Immunol., 18:143-164.

Tsunoo, H., et al., "Effects of Inerferon-$\beta$ in combination with 5-Fluorouracil on the Growth of Esophageal Cancer Cells In Vitor", Anticancer Research 21:3301-3306 (2001).

Sakai, I., et al., "Constitutive expressionof SOCS3 confers resistance to IFN-$\alpha$ in chronic myelogenous leukemia cells", The American Society of Hematology, vol. 100, No. 8, Oct. 15, 2002, XP-002323165.

Fujimoto, M., et al., "Regulation of cytokine signaling by SOCS family molecules", Trends in Immunology, vol. 24, No. 12, Dec. 2003.

* cited by examiner

MODULATION OF SOCS EXPRESSION IN THERAPEUTIC REGIMENS

CROSS REFERENCE TO RELATED APPLICATIONS

This application claims the benefit of U.S. provisional patent application Ser. No. 60/513,100, filed Oct. 21, 2003, the entire contents of which are incorporated herein by reference.

FIELD OF THE INVENTION

The invention relates to methods of treating medical conditions using cytokines. In the methods of the invention, the dose and means of administration of a cytokine are controlled in order to optimize its therapeutic effect.

BACKGROUND OF THE INVENTION

Advances in biotechnology have resulted in the development of a large number of novel therapeutic agents and methods for their use. Cytokines, polypeptides released by cells that act as mediators of a wide variety of physiological processes are particularly promising class of these novel therapeutic agents. Therapeutic methodologies employing cytokines are currently used to treat a variety of different pathological conditions including cancers as well as viral infections.

Cytokines are pleiotropic and modulate a wide variety of cellular activities. In therapeutic regimens, the effects of cytokines may not be restricted to diseased tissue but can also manifest in normal, healthy cells as well. As a result, undesirable side effects can arise during cytokine therapy, particularly when high doses are required. For example, administration of cytokines can lead to myelosuppression resulting in reduced red blood cell, white blood cell and platelet levels. Doses of cytokines can also give rise to flu-like symptoms (e.g., fever, fatigue, headaches and chills), gastrointestinal disorders (e.g., anorexia, nausea and diarrhea), dizziness and coughing. Consequently, there is a need in the art for a better understanding of the mechanisms of cytokine action and regulation so that new therapeutic methods can be developed and precisely tailored to optimize a therapeutic response while concurrently minimizing unwanted side effects.

Recently, a number of studies have focused on the mechanisms by which cytokine actions are negatively regulated by polypeptides know as "suppressors of cytokine signalling" (SOCS). Suppressors of cytokine signalling are a family of intracellular molecules including at least eight members, SOCS 1 to SOCS7 and cytokine inducible SH2-containing protein (CIS). SOCS polypeptides have been detected in various tissues and are produced in response to a large number of different cytokines. SOCS regulate the magnitude and duration of responses triggered by cytokines by inhibiting their signal transduction pathway in a classical negative feedback loop. For example, a variety of cytokines including interferons induce the expression of SOCS 1 and SOCS 3 proteins. These SOCS proteins then inhibit the activities of the cytokines that induced their expression. For articles discussing SOCS polypeptides and their mechanism of action, see, e.g. Song et al., Journal of Biological Chemistry, 273(53): 35056 (1998) Alexander et al., J. Leukocyte Biology 66: 588 (1999); Yasukawa et al., Annual Review of Immunology 18: 143-164 (2000); Chen et al., Immunity 13: 287 (2000); Nicola et al., Experimental Hematology 28: 1105 (2000); Fujimoto et al., International Immunology, 14911): 1343-1350 (2002); Crespo et al., Eur. J. Immunol. 32: 710-719 (2002); Chong et al., Diabetes 50: 2744-2751 (2001); O'keefe et al., Journal of Immunology, 166: 2260-2269 (2001); Cornish et al., Journal of Immunology, 170: 878-886 (2003); Dickensheets et al., P.N.A.S. 96: 10800-10805 (1999); Cottet et al., Journal of Biological Chemistry, 276(28): 25862-25870 (2001) and Federici et al., Journal of Immunology 168: 434 (2002), the contents of all of which are incorporated herein by reference.

At the molecular level, SOCS polypeptides bind directly to the catalytic domains of Janus kinase Oak) proteins within the cytokine receptor complex and act to impede the recruitment and phosphorylation and activation of downstream polypeptide efforts of cytokine signalling known as "signal transducers and activator of transcription" (STATs) (see, e.g. Gadina et al., Curr. Opin. Immunol. 13: 363 (2001)). The induction of SOCS by cytokines and negative regulation of cytokine signaling by SOCS have been documented in a variety of cell types (see, e.g. Sakamoto et al., Blood 92: 1668 (1998); Song et al., Journal of Biological Chemistry, 273(53): 35056 (1998); and Alexander et al., J. Leukocyte Biology 66: 588 (1999)). SOCS 1 inhibits interferon signaling by binding as a psuedosubstrate to Jak1 and Jak2, which are associated, respectively, with the IFN-R subunits. Thus disabled Jak1 and Jak2 cannot mediated STAT phosphorylation, which is necessary for the activation of γ-activated sequences (GAS) in the promoters of target genes (see, e.g. Gadina et al., Curt. Opin. Immunol. 13: 363 (2001); Yasukawa et al., Annual Review of Immunology 18: 143 (2000); and Stark et al., Annu. Rev. Biochem. 67: 227 (1998)). SOCS 3 also represses signalling induced by cytokines by similarly inhibiting STAT activation through binding to Jak kinases (see, e.g. Song et al., Journal of Biological Chemistry, 273(53): 35056 (1998)).

As noted above, the specific physiological processes associated with cytokine signalling are slowly being elucidated. In view of the current limited understanding of these processes however, medical practitioners are left to empirically determine optimal cytokine dosages and means of administration through trial and error. Unfortunately this results in less than optimal therapeutic regimens that, for example, exhibit a number of undesirable side effects which can compromise the therapeutic usefulness of such agents. Consequently, there is a need in the art for an understanding of the physiological mechanisms of cytokine action and regulation so that therapeutic methods that take these mechanisms into account can be developed. This information will allow medical personnel to design optimized therapeutic regimens that use cytokines in the treatment of various disease states. The invention disclosed herein meets this need.

SUMMARY OF THE INVENTION

The invention disclosed herein provides methods for administering therapeutically effective cytokines in which the specific dose and means of administration are precisely tailored in order to optimize a clinical outcome. Typically, the dose and means of administration of the cytokine are controlled in order to effect only a subset of the total physiological processes that are modulated by that cytokine. In illustrative embodiments of the invention, the dose and means of administration of the cytokine are controlled in a manner that controls the SOCS 1 (SEQ ID NO: 1) or SOCS 3 (SEQ ID NO: 3) mediated feedback inhibition of cytokine signalling.

In one embodiment of the invention, a human is administered a therapeutically effective amount of a cytokine capable of inducing SOCS 1 (SEQ ID NO: 1) or SOCS 3 (SEQ ID NO: 3), wherein the amount of cytokine administered is selected to be insufficient to activate feedback inhibition of the cytokine activity by SOCS 1 (SEQ ID NO: 1) or SOCS 3 (SEQ ID NO: 3) in one of the human's cells that expresses a cytokine receptor that is bound by the cytokine. In a closely related embodiment, the human is parenterally administered dose of cytokine selected to be insufficient to induce a mRNA encoding SOCS 1 (SEQ ID NO: 1) or SOCS 3 (SEQ ID NO: 3) in a cell in the human that is exposed to the parenterally administered cytokine. In illustrative embodiments of the invention, the SOCS inducing cytokine is insulin, insulin-like growth factor 1, a growth hormone, a prolactin, a interleukin-2, a interleukin-4, a interleukin-6, a interleukin-7, a interleukin-10, a interleukin-12, a LIF, a thrombopoietin, a prolactin, a stem cell factor, a erythropoietin a tumor necrosis factor or an interferon such as alpha interferon, beta interferon or gamma interferon. Optionally in such methods, the human cell is in a patient and the cytokine is administered to the patient via continuous infusion.

A related embodiment of the invention is a method of inhibiting the induction of mRNA encoding SOCS 1 (SEQ ID NO: 1) or SOCS 3 (SEQ ID NO: 3) polypeptide in a human cell exposed to a therapeutically effective amount of a cytokine capable of inducing the SOCS 1 or SOCS 3 mA, the method comprising the steps of determining the minimal amount of cytokine that will induce mRNA encoding SOCS 1 or SOCS 3 in the human cell; and then exposing the human cell to a therapeutically effective amount of a SOCS inducing cytokine that is less than the minimal amount of cytokine that will induce mRNA encoding SOCS 1 or SOCS 3 in the human cell, so that the induction of mRNA encoding SOCS 1 or SOCS 3 in the human cell is inhibited. Optionally, the amount of cytokine administered is the maximal dose of SOCS inducing cytokine that fails to induce mRNA encoding SOCS 1 (SEQ ID NO: 1) or SOCS 3 (SEQ ID NO: 3). In one such embodiment, the amount of cytokine administered is approximately 95%-99% of the minimal amount of cytokine that is required to induce SOCS 1 or SOCS 3. Alternatively, the amount of cytokine administered is approximately 10%, 20%, 30%, 40%, 50% 60%, 70%, 80% or 90% of the minimal amount of cytokine that is required to for the sustained induction of SOCS 1 or SOCS 3.

A related embodiment of the invention is a method of inhibiting the sustained transcription of mRNA encoding SOCS 1 (SEQ ID NO: 1) or SOCS 3 (SEQ ID NO: 3) polypeptide in a human cell exposed to a therapeutically effective amount of a cytokine capable of inducing the sustained transcription of SOCS 1 or SOCS 3 mRNA (i.e. where the transcription does not result in a mere transient increase in mRNA encoding SOCS 1 or SOCS 3), the method comprising the steps of determining the minimal amount of cytokine that will induce the sustained transcription of mRNA encoding SOCS 1 or SOCS 3 in the human cell; and then exposing the human cell to a therapeutically effective amount of a SOCS inducing cytokine that is less than the minimal amount of cytokine that will induce the sustained transcription of mRNA encoding SOCS 1 or SOCS 3 in the human cell, so that the sustained transcription of mRNA encoding SOCS 1 or SOCS 3 in the human cell is inhibited. Preferably, the mRNA encodes SOCS 1.

Yet another embodiment of the invention is a method of controlling the biological activity of SOCS 1 (SEQ ID NO: 1) or SOCS 3 (SEQ ID NO: 3) in a human cell exposed to a therapeutically effective amount of a cytokine capable of inducing SOCS 1 or SOCS 3 biological activity, the method comprising the steps of determining the minimal amount of SOCS inducing cytokine that will induce SOCS 1 or SOCS 3 biological activity in the human cell; and then exposing the human cell to a therapeutically effective amount of a SOCS inducing cytokine that is less than the amount determined to be the minimal amount of SOCS inducing cytokine that will induce SOCS 1 or SOCS 3 biological activity in the human cell, so that the biological activity of SOCS 1 or SOCS 3 in a human cell is controlled. In one such embodiment, the dose of cytokine is an amount of SOCS inducing cytokine that will fail to induce any SOCS 1 or SOCS 3 biological activity in the human cell. In an alternative embodiment, the dose of cytokine is an amount of SOCS inducing cytokine that will fail to induce sustained SOCS 1 or SOCS 3 biological activity in the human cell. Optionally, the SOCS polypeptide is SOCS 1.

In the above described methods for controlling the biological activity of SOCS 1 (SEQ ID NO: 1) or SOCS 3 (SEQ ID NO: 3), the SOCS inducing cytokine used in the method is optionally a human growth hormone, a prolactin, a interleukin such as interleukin-2, interleukin-4, interleukin-6, interleukin-7, interleukin-10 or interleukin-12, a LIF, a TPO, a prolactin, a stem cell factor, a erythropoietin a tumor necrosis factor or an interferon such as alpha interferon, beta interferon or gamma interferon. Understandably the methods of the invention are applicable to all pleiotropic SOCS inducing cytokines where the dose necessary to effect at least one therapeutically desired activity is less that the dose necessary to induce a biological activity of SOCS 1 (SEQ ID NO: 1) and/or SOCS 3 (SEQ ID NO: 3). Optionally, the human cell is in a patient and the cytokine is administered to the patient via continuous infusion.

In certain embodiments of the invention, the duration of the treatment is predetermined. In an illustrative embodiment, the duration of the treatment is at least 1, 2, 3, 4, 5, 6, 7, 8, 9, 10, 11 or 12 weeks. Alternatively, the duration of the treatment is dependent upon the observation of a change in some factor associated with the pathological condition such as analyte concentration (e.g. blood sugar in the metabolic diseases such as diabetes), tumor size (e.g. in cancer) or viral titer (e.g. in viral infection). For example, in certain embodiments of the invention, the method of treating a viral infection results in a 50%, 90% or 95% decrease in the level of virus particles and/or a viral biological activity in the human.

In additional embodiments, the invention provides articles or manufacture and/or kits comprising a container comprising a cytokine capable of inducing SOCS 1 or SOCS 3 biological activity as described herein and instructions for using the cytokine; such as to treat a disorder against which the cytokine is effective. Optionally, the disorder is a metabolic disease, a cancer or a viral infection.

DETAILED DESCRIPTION OF THE INVENTION

Figure 1:
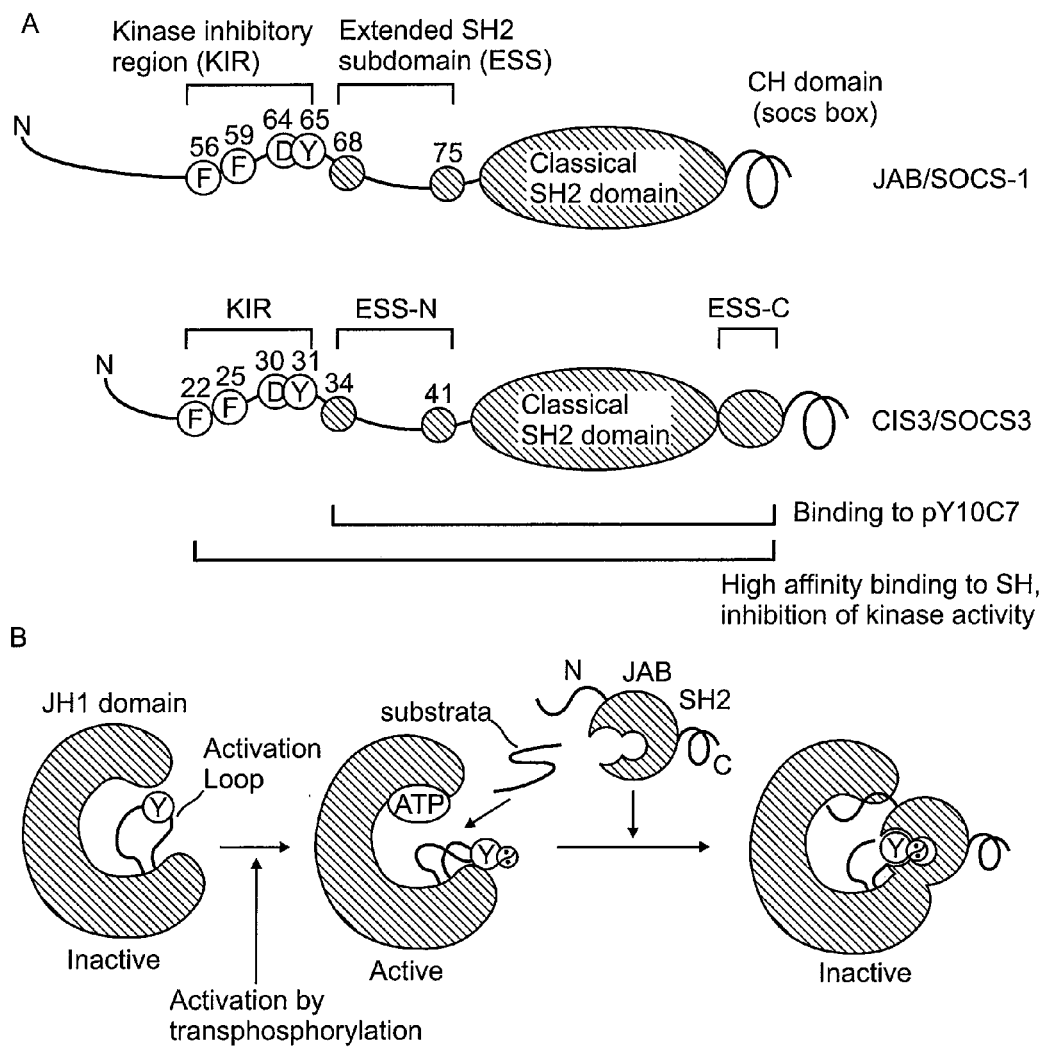
FIG. 1 provides a structure and model of kinase inhibition by JAB/SOCS-1 and CIS3/SOCS-3. (A) Schematic model of the functions of SOCS-1 and SOCS-3 domains. Essential amino acids in the kinase inhibitory region (KIR) and the extended SH2 subdomain are in bold circles. (B) The model of JH1 activation and inhibition by SOCS-1. Binding of SOCS-1 to the activation loop prevents the access of substrates and/or ATP to the catalytic pocket. See, e.g. Yasukawa et al., Annual Review of Immunology 18: 143-164 (2000) which is incorporated herein by reference.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in see Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Definitions

The term "administer" means to introduce a formulation of the present invention into the body of a patient in need thereof to treat a disease or condition.

The term "continuous infusion system" refers to a device for continuously administering a fluid to a patient parenterally for an extended period of time or for, intermittently administering a fluid to a patient parenterally over an extended period of time without having to establish a new site of administration each time the fluid is administered. The fluid contains a therapeutic agent or agents. The device typically has a reservoir for storing the fluid before it is infused, a pump, a catheter, or other tubing for connecting the reservoir to the administration site via the pump, and control elements to regulate the pump. The device may be constructed for implantation, usually subcutaneously. In such a case, the reservoir will usually be adapted for percutaneous refilling.

The term "treating" refers to the management and care of a patient having a pathology such as cancer, a viral infection or other condition for which administration of a SOCS 1 or SOCS 3 inducing cytokine is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder. As used herein, "treatment" or "therapy" refer to both therapeutic treatment and prophylactic or preventative measures.

The term "therapeutically effective amount" refers to an amount of an agent (e.g. cytokine) effective to treat at least one sign or symptom of a disease or disorder in a mammal. Amounts of an agent for administration may vary based upon the desired activity, the diseased state of the mammal being treated, the dosage form, method of administration, patient factors such as the patient's sex, weight and age, the underlying causes of the condition or disease to be treated, the route of administration and bioavailability, the persistence of the administered agent in the body, the formulation, and the potency of the agent. It is recognized that a therapeutically effective amount is provided in a broad range of concentrations. Such range can be determined based on in vitro and/or in vivo assays.

As used herein, the term "synergy" or "synergism" or "synergistically" refers to the interaction of two or more agents so that their combined effect is greater than the sum of their individual effects.

The term "cytokine" is a generic term for a class of polypeptides released by cells that act as mediators of a wide variety of physiological processes. Examples of such cytokines ate lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; gonadotropin-associated peptide; inhibin; activin; vascular endothelial growth factor; integrin; thrombopoietin (IPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). The term "insulin" includes those mammalian insulin proteins having a biological activity that allows them to be used in the treatment of diabetes such as human insulin and insulins from non-human mammals as well as variants of human insulin (e.g. porcine insulin and LISPRO insulin). The structure of human insulin is disclosed in Nature 187,483 (1960). A review of the research, development, and recombinant production of human insulin is found in Science 219, 632-637 (1983). See also U.S. Pat. No. 4,652,525 (rat insulin) and U.S. Pat. No. 4,431,740 (human insulin). This term includes human insulin variants known in the art, for example the variant wherein Pro at position B28 is substituted with Asp, Lys, Leu, Val, or Ala, and wherein position B29 is Lys or is substituted with Pro; AlaB26-human insulin, des(B28-B30) human insulin; and des(B27) human insulin. Such monomeric insulin analogs are disclosed in U.S. Pat. No. 5,514,646, WO 99/64598, WO 99/6459A2 and WO 96/10417A1. The term "interferon" as used herein means the family of highly homologous species-specific proteins that inhibit viral replication and cellular proliferation and modulate immune response. Human interferons are grouped into three classes based on their cellular, origin and antigenicity: α-interferon (eukocytes), β-interferon (fibroblasts) and γ-interferon (T cells). Recombinant forms of each group have been developed and are commercially available. Subtypes in each group are based on antigenic/structural characteristics. A number of α-interferons (grouped into subtypes) having distinct amino acid sequences have been identified by isolating and sequencing DNA encoding these peptides. Both naturally occurring and recombinant α, β and γ-interferons may be used in the practice of the invention. As used herein, the term cytokine includes proteins from natural sources or from recombinant cell culture and biologically active equivalents of the native sequence cytokines.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, ovarian cancer, colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) can also be uracil (U); this definition pertains to the differences between the chemical structures of DNA and RNA, in particular the observation that one of the four major bases in RNA is uracil (U) instead of thymidine (T).

As used herein, the term "polypeptide" means a polymer of at least about 4, 5, 6, 7, or 8 amino acids. Throughout the specification, standard three letter or single letter designations for amino acids are used. In the art, this term is often used interchangeably with "protein".

As used herein, the terms "hybridize", "hybridizing", "hybridizes" and the like, used in the context of polynucleotides, are meant to refer to conventional hybridization conditions, preferably such as hybridization in 50% formamide/ 6×SSC/0.1% SDS/100 µg/ml ssDNA, in which temperatures for hybridization are above 37 degrees C and temperatures for washing in 0.1×SSC/0.1% SDS are above 55 degrees C.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by but not limited to those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The term "antibody" when used for example in reference to an "antibody capable of binding SOCS 1 or SOCS 3 polypeptides" is used in the broadest sense and specifically covers intact monoclonal antibodies, polyclonal antibodies, multispecific antibodies (e.g. bispecific antibodies) formed from at least two intact antibodies, and antibody fragments so long as retain their ability to immunospecifically recognize a target polypeptide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulin. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al. *J. Mol. Biol.*, 222:581-597 (1991), for example.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In illustrative embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

Physiological Mechanisms Relating to the Invention

The invention disclosed herein provides methods for administering therapeutically effective cytokines in which the specific dose and means of administration are controlled in order to optimize a clinical outcome. It is well known in the art that cytokines are pleiotropic, that is they are capable of modulating a variety of disparate cellular activities. As different cellular activities are modulated by differing concentrations of a cytokine, this pleiotropism should be considered when considering the dose and schedule of a therapeutic agent. This need to consider the pleiotropic effects of a therapeutic agent is supported by both mechanistic and empirical observations. For example, the interferon mediated downregulation of angiogenesis-related genes observed when using interferon to treat bladder cancer is dependent on optimization of biological dose and schedule. In this context, the antiangiogenic activity of interferon cytokine is shown to be dependent on frequent administration of optimal biological dose and not maximal tolerated dose (see, e.g. Slaton et al., Clin Cancer Res. 1999 October; 5(10):2726-34).

Without being bound by a specific scientific theory, the disclosure provided herein teaches methods that take the pleiotropic mechanisms of cytokine action and regulation into account in order to optimize therapeutic regimens. For example, as disclosed herein, a general paradigm in cytokine signal transduction is cytokine-induced feedback inhibition and the desensitization of signaling. As this feedback inhibition and desensitization of cytokine signaling can be dose dependent, therapeutic regimens that fail to take these physiological feedback processes into account (i.e. therapeutic regimens involving high doses of cytokines such as bolus therapy) can in fact inhibit the biological activities of the therapeutic cytokine and therefore fail to provide an optimal therapeutic regimen. See, e.g. Friederichs et al, Eur J Biochem. 2001 December; 268(24):6401-7; Hu et al., Nature Immunology 3(9): 859-866 (2002); Ronn et al., Mol Endocrinol. 2002 September; 16(9):2124-34:

One mechanism of cytokine-induced feedback inhibition and desensitization of signaling involves polypeptides know as "suppressors of cytokine signalling" (SOCS). SOCS regulate the magnitude and duration of responses triggered by cytokines by inhibiting their signal transduction pathway in a classical negative feedback loop (see, e.g. Song et al., Journal of Biological Chemistry, 273(53): 35056 (1998); Alexander et al., J. Leukocyte Biology 66: 588 (1999); Yasukawa et al., Annual Review of Immunology 18: 143 (2000); Chen et al., Immunity 13: 287 (2000); Nicola et al., Experimental Hematology 28: 1105 (2000) and Federici et al., Journal of Immunology 168: 434 (2002)). For example, cytokines can induce the expression of SOCS 1 and SOCS 3 proteins when they bind to their cognate receptors on the surfaces of cells. At the appropriate concentrations of cytokines, these SOCS proteins can then inhibit the activities of the very cytokines that induced their expression (see, e.g. Song et al., Journal of Biological Chemistry, 273(53): 35056 (1998)), in either a transient or sustained manner depending upon cytokine dose.

Interestingly, it is observed that low doses of a cytokine such as interferon that do not themselves activate every single mechanism and/or aspect associated with this cytokine's signalling through its cognate receptor can function to sensitize subsequent cellular signalling in response to that cytokine. This dose dependent mechanism of interferon signaling sensitization involves increasing STAT1 expression in the absence of feedback inhibition by SOCS 1 (see, e.g. Hu et al., Nature Immunology 3(9): 859-866 (2002)). Specifically, low doses of interferon induce transient increases in SOCS mRNA that return to baseline amounts after about 4 hours and remain low during the remainder of the priming period. In contrast, with high concentrations of interferon the increase in mRNA levels is sustained, with SOCS mRNA continuing to increase for 24 hours and remaining elevated for the duration of the priming period. STAT mRNA is elevated in a sustained manner with both priming and activating concentrations of interferon. Thus, priming cells with low doses of interferon results in high expression of STAT in the absence of induction of feedback inhibition by SOCS. The sustained increase in STAT1 mRNA indicates that activation of STAT1 gene expression contributes to increased amounts of STAT1. Both the combination of sustained expression of STAT1 mRNA and the stability of STAT1 protein contribute to the increase in STAT1 protein observed during priming. This increase in STAT1 protein observed during priming then serves to further the activation and potentiation of cytokine signalling.

As noted above, low priming doses of interferons capable of activating sustained STAT1 expression do not effectively activate feedback inhibition by SOCS 1. The sensitivity of cells to interferons is regulated by the opposition of STAT1 and SOCS proteins that are expressed at different relative amounts, depending upon the intensity and/or duration of an activating stimulus (i.e. exposure to a cytokine). In this context, high expression of STAT1 will overcome or balance inhibition by SOCS proteins. As the intensity and/or duration of an activating stimulus can be controlled by controlling both the dose and means of administration of a cytokine, an understanding of the above-noted mechanisms of cytokine signalling allows practitioners to control certain cytokine mediated physiological processes in a manner that optimizes a therapeutic regimen that employs SOCS inducing cytokines.

The disclosure provided herein provides methods for administering SOCS inducing cytokines in which the biological dose and schedule of administration are controlled in a manner designed to control the expression of polypeptides known to modulate physiological responses triggered by these cytokines (e.g. by inhibiting their signal transduction pathway in a negative feedback loop). The methods disclosed herein can be used to overcome problems in the art that are associated with the administration of suboptimally high doses of cytokine that can trigger SOCS mediated feedback inhibition, particularly sustained feedback inhibition (e.g. as can occur in cytokine bolus therapy). In addition, this disclosure overcomes problems in the art that are associated with methods that may employ suboptimally low doses interferon that are designed to eliminate or diminish side effects normally associated with cytokine administration but which also fail to provide a patient with a optimized therapeutic dose (e.g. a maximally therapeutic dose that avoids sustained SOCS 1 or SOCS 3 induction).

The disclosure provided herein teaches that, in regimens where is desirable to maximize cytokine signalling by avoiding cytokine mediated induction of SOCS, one can employ a therapeutic regimen specifically tailored for this purpose. In illustrative embodiments of the invention, the dose and means of administration of the cytokine are controlled in a manner that avoids or inhibits the SOCS 1 (SEQ ID NO: 1) or SOCS 3 (SEQ ID NO: 3) mediated feedback inhibition of cytokine signalling. A specific embodiment is a method of controlling the biological activity of SOCS 1 (SEQ ID NO: 1) or SOCS 3 (SEQ ID NO: 3) in a human cell exposed to a therapeutically effective amount of a cytokine capable of inducing SOCS 1 or SOCS 3 biological activity in the cell, the method comprising the steps of determining the minimal amount of SOCS inducing cytokine that will induce SOCS 1 or SOCS 3 biological activity in the human cell; and then exposing the human cell to an therapeutically effective amount of a SOCS inducing cytokine that is less than the amount capable of inducing SOCS 1 or SOCS 3 biological activity so that the induction of SOCS 1 or SOCS 3 biological activity in the human cell is controlled. In one illustrative embodiment of the invention, a continuous dose infusion of a cytokine such as an interferon is used to treat a cancer. In another illustrative embodiment of the invention, a continuous dose infusion of a cytokine such as an interferon is used to treat a viral infection.

Typical Methodologies for Practicing Embodiments of the Invention

The methods disclosed herein may be employed in protocols for treating pathological conditions in mammals such as viral infection and cancer. For example in one embodiment of the invention, an infusion of IFN-γ and/or IFN-β is used to treat hepatitis B viral infection (see, e.g. Musch et al., Z Gastroenterol. 2003 May; 41(5):425-8). In another embodiment of the invention, an infusion of IFN-γ is used to treat a cancer (see, e.g. Tsunoo et al., Anticancer Res. 2001 September-October; 21(5):3301-6). In typical methods, an interferon is administered to a mammal, alone or in combination with still other therapeutic agents or techniques. Diagnosis in mammals of the various pathological conditions described herein can be made by the skilled practitioner.

Embodiments of the invention include methods of treating a hepatitis viral infection in a human comprising continuously parenterally administering an interferon to the human. Interferons are a subclass of cytokines that exhibit both antiviral and antiproliferative activity. On the basis of biochemical and immunological properties, the naturally-occurring human interferons are typically grouped into three classes: interferon-alpha (leukocyte), interferon-beta (fibroblast) and interferon-gamma (immune). A number of alpha interferons (grouped into subtypes) having distinct amino acid sequences have been identified by isolating and sequencing DNA encoding these polypeptides. Alpha interferons have received considerable attention as potential therapeutic agents due to their antiviral and antitumor growth inhibition. Interferon polypeptides for use in the methods disclosed herein include interferon variants, interferon fragments, analogues, and derivatives. By "analogues" is intended analogues of either interferon or an interferon fragment that comprise a native interferon sequence and structure, having one or more amino acid substitutions, insertions, or deletions. By "derivatives" is intended any suitable modification of interferon, interferon fragments, or their respective analogues, such as glycosylation, phosphorylation, or other addition of foreign moieties (e.g. Pegylation as described below), so long as the desired activity is retained. Methods for masking interferon fragments, analogues, and derivatives are available in the art. Interferons are described in U.S. Pat. Nos. 4,695,623, 5,372,808 and 5,541,293.

As used herein, a cytokine gene and cytokine protein includes the human cytokine genes and proteins specifically described herein, as well as biologically active structurally and/or functionally similar variants or analog of the foregoing. Cytokine peptide analogs generally share at least about 50%, 60%, 70%, 80%, 90% or more amino acid homology (using BLAST criteria). For example, % identity values may be generated by WU-BLAST-2 (Altschul et al., 1996, Methods in Enzymology 266:460-480. Cytokine nucleotide analogs preferably share 50%, 60%, 70%, 80%, 90% or more nucleic acid homology (using BLAST criteria). In some embodiments, however, lower homology is preferred so as to select preferred residues in view of species-specific codon preferences and/or optimal peptide epitopes tailored to a particular target population, as is appreciated by those skilled in the art. Fusion proteins that combine parts of different cytokine proteins or fragments thereof, as well as fusion proteins of a cytokine protein and a heterologous polypeptide are also included. Such cytokine proteins are collectively referred to as the cytokine-related proteins, the proteins of the invention, or cytokines.

The term "variant" refers to a molecule that exhibits a variation from a described type or norm, such as a protein that has one or more different amino acid residues in the corresponding position(s) of a specifically described protein. An analog is an example of a variant protein. As used herein, the cytokine-related gene and cytokine-related protein includes the cytokine genes and proteins specifically described herein, as well as structurally and/or functionally similar variants or analog of the foregoing cytokine peptide analogs generally share at least about 50%, 60%, 70%, 80%, 90% or more amino acid homology (using BLAST criteria). Cytokine nucleotide analogs preferably share 50%, 60%, 70%, 80%, 90% or more nucleic acid homology (using BLAST criteria). In some embodiments, however, lower homology is preferred so as to select preferred residues in view of species-specific codon preferences and/or optimal peptide epitopes tailored to a particular target population, as is appreciated by those skilled in the art.

Embodiments of the invention disclosed herein include a wide variety of art-accepted variants or analogs of cytokine proteins such as polypeptides having amino acid insertions, deletions and substitutions. Cytokine variants can be made using methods known in the art such as site-directed mutagenesis, alanine scanning, and PCR mutagenesis. Site-directed mutagenesis (Carter et al., *Nucl Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the cytokine variant DNA. Resulting mutants can be tested for biological activity. Sites critical for binding can be determined by structural analysis such as crystallization, photoaffinity labeling, or nuclear magnetic resonance. See, deVos et al. (1992) Science 255:306 and Smith et al. (1992:) J. Mol. Biol. 224:899.

As is known in the art, conservative amino acid substitutions can frequently be made in a protein without altering the functional activity of the protein. Proteins of the invention can comprise conservative substitutions. Such changes typically include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations, in which the significant feature of the amino acid residue is its charge and the differing pK's of these two amino acid residues are not significant. Still other changes can be considered "conservative" in particular environments.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

Cytokines useful in the methods of the present invention must possess a desired biological activity of the native protein, for example one of their antiviral, immunomodulatory and/or antiproliferative activities (see, e.g. De Maeyer et al., (1988) Cytokines and Other Regulatory Cytokines, John Wiley and Sons, New York). Other cytokines useful in methods of the present invention must possess an ability to induce a mRNA encoding SOCS 1 (SEQ ID NO: 1) or SOCS 3 (SEQ ID NO: 3) and/or the ability to induce the biological activity of SOCS 1 (SEQ ID NO: 1) or SOCS 3 (SEQ ID NO: 3) in a human cell.

In illustrative embodiments of the invention, the cytokine used in the therapeutic regimen is unmodified. However, modified molecules such as polyol conjugated cytokines are contemplated as alternative embodiments of the invention. Consequently, illustrative methods of producing cytokines covalently attached (hereinafter "conjugated") to one or more chemical groups are disclosed below. Chemical groups suitable for use in an cytokine conjugate of the present invention are preferably not significantly toxic or immunogenic. The chemical group is optionally selected to produce a cytokine conjugate that can be stored and used under conditions suitable for storage. A variety of exemplary chemical groups that can be conjugated to polypeptides are known in the art and include for example carbohydrates, such as those carbohydrates that occur naturally on glycoproteins, and non-proteinaceous polymers, such as polyols (see, e.g., U.S. Pat. No. 6,245,901).

A polyol, for example, can be conjugated to polypeptides such as an cytokine at one or more amino acid residues, including lysine residues, as is disclosed in WO 93/00109. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to a polypeptide is termed "pegylation." However, those skilled in the art recognize that other polyols, such as, for example, poly(propylene glycol) and polyethylene-polypropylene glycol copolymers, can be employed using the techniques for conjugation described herein for PEG. Illustrative examples of cytokines conjugated with PEG are shown, for example, in U.S. Pat. Nos. 5,795,569; 4,902,502; Wang et al., Biochemistry 2000, 39, 10634-10640; Leong et al., Cytokine 2001, 16(3): 24-36; and Kozlowski et al., BioDrugs 2001; 15(7): 419-429.

The cytokine polypeptides, cytokine polypeptide variants, cytokine polypeptide fragments, cytokine polynucleotides encoding said polypeptides, variants and fragments, and the cytokine agents useful in the methods of the invention can be incorporated into pharmaceutical compositions or formulations suitable for administration into a mammal. In an illustrative embodiment of the invention, the mammal is a human. Such compositions typically comprise at least one cytokine polypeptide, cytokine polypeptide variant, cytokine polypeptide fragment, cytokine polynucleotide encoding said polypeptide, variant or fragment, an cytokine agent, or a combination thereof, and a pharmaceutically acceptable carrier. Methods for formulating the cytokine compounds of the invention for pharmaceutical administration are known to those of skill in the art. See, for example, Remington: The Science and Practice of Pharmacy, 19$^{th}$ Edition, Gennaro (ed.) 1995, Mack Publishing Company, Easton, Pa. Formulations to be used for in vivo administration should be sterile. This is readily accomplished by filtration through sterile filtration membranes.

As noted above, formulations used in the methods of the invention may contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The cytokine polypeptide may be administered to the mammal in combination with effective amounts of one or more other therapeutic agents. The one or more other therapeutic agents or therapies may include, but are not limited to 5-fluorouracil or ribavirin. Fluorouracil and ribavirin are nucleoside analogs that modulates a number of physiological processes including cell growth and/or the balance of the TH1/Th2 response. See, e.g. Goodman & Gilman's "The Pharmacological Basis of Therapeutics", Ninth Edition, (1996) McGraw Hill, N.Y., at pages 1214-1215 and the 1999 Physicians Desk Reference at pages 1382-1384.

The therapeutic cytokines and related therapeutic molecules (e.g. 5-fluorouracil) that are useful in the method of the invention are preferably administered in a carrier. The molecules can be administered in a single carrier, or alternatively, can be included in separate carriers. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the carrier to render the formulation isotonic. Examples of the carrier include saline, Ringer's solution and dextrose solution. The pH of the solution is preferably from about 5 to about 8, and more preferably from about 7.4 to about 7.8. It will be apparent to those persons skilled in the art that certain carriers may be more preferable depending upon, for instance, the route of administration and concentration of agent being administered. The carrier may be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

Optionally the cytokines used in the methods of the invention combined with at pharmaceutically acceptable carrier. The term "pharmaceutically acceptable carrier" is used according to its art accepted meaning and is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration.

The pharmaceutical compositions of the invention comprising cytokine polypeptides, cytokine polypeptide variants, cytokine polypeptide fragments, polynucleotides encoding said cytokine polypeptides, variants and fragments, as well as cytokine agents, as defined above, are administered in therapeutically effective amounts. The "therapeutically effective amount" refers to a nontoxic dosage level sufficient to induce a desired biological result (e.g. a diminution of the severity of the symptoms associated with a pathological condition such as cancer or a viral infection).

Therapeutic compositions of the cytokine can be prepared by mixing the desired cytokine having the appropriate degree of purity with optional pharmaceutically acceptable carriers, excipients, or stabilizers (*Remington's Pharmaceutical Sciences,* 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight 0ess than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances. Carriers for topical or gel-based forms include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols.

Solutions or suspensions used for administering a cytokine can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose.

As used herein, an optimized dose of cytokine is an amount which, taking the route of administration into account is controlled in order to effect only a subset of the total physiological processes that are modulated by that cytokine. In illustrative embodiments of the invention, the cytokine is administered via continuous infusion therapy and the dose is selected to avoid or inhibit the SOCS 1 (SEQ ID NO: 1) or SOCS 3 (SEQ ID NO: 3) mediated feedback inhibition of cytokine signalling. The terms "continuous administration" and "continuous infusion" are used interchangeably herein and mean maintaining a steady state serum level of the cytokine throughout the course of the treatment period. This can be accomplished by constantly or repeatedly injecting substantially identical amounts of an agent, e.g., at least every hour, 24 hours a day, seven days a week, such that a steady state serum level is achieved for the duration of treatment.

The dose of cytokine and route of administration may vary depending on the desired effect and/or outcome. Preferably the cytokine is insulin and is administered via a continuous infusion pump. Typically the dose and route of administration is selected to provide a therapeutically effective amount of insulin such as a low priming does of insulin that is capable of activating STAT expression yet does not effectively activate feedback inhibition by SOCS 1 or SOCS 3 (see, e.g. Hu et al., Nature Immunology, 3(9): 859-866 (2002). In illustrative embodiments of the invention, such an optimized dose of insulin is continuously administered to a mammal, in particular a human patient, exhibiting one or more of the above signs or symptoms of viral infection in an amount and for a period of time sufficient to eliminate or at least alleviate one or more of the signs or symptoms associated with this disease.

Continuous optimized dose insulin administration may be by subcutaneous or intravenous injection at appropriate intervals, e.g. at least hourly, for an appropriate period of time in an amount which will facilitate or promote a desired therapeutic effect. In illustrative embodiments of the invention, the cytokine is administered via an infusion pump such as a Medtronic MiniMed model 508 infusion pump. The Model 508 is currently a leading choice in insulin pump therapy, and has a long history of safety, reliability and convenience. Typically the pump includes a small, hand-held remote programmer, which enables diabetes patients to program cytokine delivery without accessing the pump itself Continuous subcutaneous administration can also by accomplished by, for example, a pulsatile electronic syringe driver (Provider Model PA 3000, Pancretec Inc., San Diego Calif.), a portable syringe pump such as the Graseby model MS 1 6A (Graseby Medical Ltd., Watford, Herts England), or a constant infusion pump such as the Disetronic Model Panomat C-S. Osmotic pumps, such as that available from Alza, may also be used. Since use of continuous subcutaneous injections allows the patient to be ambulatory, it is preferred over use of continuous intravenous injections.

Formulations which simulate a constant optimized dose injection, such as but not limited to long-acting cytokine-polymer conjugates and various-sustained release formulations, are also contemplated for use. Preferred routes of administration include parenteral, e.g., intravenous, intradermal, intramuscular and subcutaneous administration. Solutions or suspensions used for parenteral, intradermal, or subcutaneous application can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. Regimens of administration may vary. Such regimens can vary depending on the severity of the disease and the desired outcome. Following administration of a interferon polypeptide to the mammal, the mammal's physiological condition can be monitored in various ways well known to the skilled practitioner familiar with the hallmarks of viral infection or cancer progression, or alternatively by monitoring the effects of administration of interferon on SOCS mRNA levels and/or SOCS biological activity.

Following administration of a cytokine to the mammal, the mammal's physiological condition can be monitored in various ways well known to the skilled practitioner. The therapeutic effects of the interferon polypeptides of the invention can be examined in in vitro assays and using in vivo animal models. A variety of well known animal models can be used to further understand the role of the interferon in the development and pathogenesis of viral infection, and to test the efficacy of the candidate therapeutic agents.

As is apparent from the disclosure provided herein, the field of the invention pertains to methods of modulating the transcription and/or biological activity of SOCS 1 (SEQ ID NO: 1) and/or SOCS 3 (SEQ ID NO: 3) in a manner that facilities the use of SOCS inducing cytokines in therapeutic regimens. As is known in the art, these SOCS polypeptides regulate the magnitude and duration of responses triggered by cytokines by inhibiting their signal transduction pathway in a negative feedback loop. As this feedback mechanism is common to a variety of different cytokines which have very different primary activities, one of skill in the art will understand that the methods of the invention are not in a field of use pertaining to a single cytokine. Instead, scope of the field of the instant invention pertains to all cytokines where the binding of the cytokine to its cognate receptor a cell induces the transcription and/or biological activity of SOCS 1 (SEQ ID NO: 1) and on/or SOCS 3 (SEQ ID NO: 3) and this induction can be controlled in the cell by controlling a therapeutically effective amount of SOCS inducing cytokine that the cell is exposed to. Moreover, as a wide variety of therapeutic regimens involve the binding of a cytokine to its cognate receptor and the subsequent induction of the cytokine's biological activity, artisans will understand that the methods of the invention are not in a field of use pertaining to a single pathology and instead pertain to all pathological conditions where the modulation of the transcription and/or biological activity of SOCS 1 (SEQ ID NO: 1) and/or SOCS 3 (SEQ ID NO: 3) can facilitate the therapeutic effect(s) of a SOCS inducing cytokine.

Illustrative examples of SOCS inducing cytokines that is used in a therapeutic regimens are interferon alpha, beta and gamma, cytokines which are used to treat cancers such colon and head and neck cancers as well as viral infections such as chronic hepatitis B. In the case of cancer, a therapeutically effective amount of the drug may reduce the cancer cell count (e.g. tumor size) in the individual and/or relieve to some extent one or more of the signs or symptoms associated with the cancer. In the case of chronic hepatitis infection, a therapeutically effective amount of the drug may reduce the numbers of viral particles detectable in the individual and/or relieve to some extent one or more of the signs or symptoms associated with the disorder. In particular, a person suffering from chronic hepatitis infection may exhibit one or more of the following signs or symptoms: (a) elevated serum alanine aminotransferase (ALT), (b) positive test for hepatitis antigens (e.g. delta particle) and/or anti-hepatitis antibodies, (c) presence of virus as demonstrated by a positive test for viral RNA, (d) clinical stigmata of chronic liver disease, (e) hepatocellular damage. Such criteria may not only be used to diagnose hepatitis, but can be used to evaluate a patient's response to drug treatment. Elevated serum alanine aminotransferase (ALT) and aspartate aminotransferase (AST) are known to occur in uncontrolled hepatitis, and a complete response to treatment is generally defined as the normalization of these serum enzymes, particularly ALT (Davis et al., 1989, New Eng. J. Med. 321:1501-1506). ALT is an enzyme released when liver cells are destroyed and is symptomatic of hepatitis infection. Interferon causes synthesis of the enzyme 2',5'-oligoadenylate synthetase (2'5'OAS), which in turn, results in the degradation of the viral mRNA. Houglum, 1983, Clinical Pharmacology 2:20-28. Increases in serum levels of the 2'5'OAS coincide with decrease in ALT levels. In order to follow the course of hepatitis replication in subjects in response to drug treatment, hepatitis RNA may be measured in serum samples by, for example, a nested polymerase chain reaction assay that uses two sets of primers derived from a hepatitis genome. Farci et al., 1991, New Eng. J. Med. 325: 98-104. Ulrich et al., 1990, J. Clin. Invest., 86:1609-1614. Histological examination of liver biopsy samples may be used as a second criteria for evaluation. See, e.g., Knodell et al., 1981, Hepatology 1:431-435, whose Histological Activity Index (portal inflammation, piecemeal or bridging necrosis, lobular injury and fibrosis) provides a scoring method for disease activity.

Illustrative Embodiments of the Invention

In the invention disclosed herein, the dose and means of administration of a cytokine are controlled in order to effect only a subset of the total physiological processes that are modulated by that cytokine. In one such embodiment of the invention, the human is parenterally administered an amount of cytokine selected to be insufficient to activate sustained feedback inhibition of that cytokine's activity by SOCS 1 (SEQ ID NO: 1) or SOCS 3 (SEQ ID NO: 3) in a cell in the human that is exposed to the parenterally administered cytokine. In a closely related embodiment, the human is parenterally administered an amount of cytokine selected to be insufficient to induce a mRNA encoding SOCS 1 (SEQ ID NO: 1) or SOCS 3 (SEQ ID NO: 3) in a cell in the human that is exposed to the parenterally administered cytokine.

Methods for examining the induction of mRNAs such as those encoding mRNA encoding SOCS 1 (SEQ ID NO: 1) and/or SOCS 3 (SEQ ID NO: 3) are also well known in the art. SOCS mRNA in a sample can be analyzed by a number of means well known in the art, including without limitation, in situ hybridization, RT-PCR analysis, and tissue array analysis. Typical protocols for evaluating the status of the SOCS gene and gene products are found, for example in Ausubel et al. eds., 1995, Current Protocols In Molecular Biology, Units 2 (Northern Blotting) and 18 (PCR Analysis). Thus, the level of SOCS mRNA in a biological sample is evaluated by various methods utilized by skilled artisans including, but not limited to Northern analysis and/or PCR analysis of SOCS mRNA (to examine, for example expression levels of SOCS mRNAs).

A variety of well known pharmacokinetic and/or pharmacodynamic models that are known in the art can be used to facilitate the methods disclosed herein. For example, assays which examine for human cells that are exposed to a series of cytokine dilutions can be used to generate dose response data which identifies cytokine concentrations that are insufficient and/or sufficient to activate feedback inhibition of cytokine activity by SOCS 1 (SEQ ID NO: 1) or SOCS 3 (SEQ ID NO: 3). For example, Song et al., teach assays which examine the ability of SOCS polypeptides to inhibit the tyrosine phosphorylation and nuclear translocation of STAT 1 in response to interferons (see, e.g. Song et al., Journal of Biological chemistry, 273(52): 35056-35062 (1998)). Hu et al., Nature Immunology 3(9): 859-866 (2002)) also teach methods of examining the biological activity of SOCS via assays such as immunoblotting as well as the metabolic labeling of STAT1.

It is well within the ordinary skill of the art to modify a route of administration and dosage regimen of a particular cytokine in order to manage the pharmacokinetics of the cytokine in a manner that effects a specific physiological response in patients. Simple in vitro assays employing human cells exposed to a series of cytokine dilutions can be used to generate dose response data pertinent to specific factors such as the concentration of a particular cytokine that is insufficient and/or sufficient to induce an mRNA encoding SOCS 1 (SEQ ID NO: 1) and/or SOCS 3 (SEQ ID NO: 3). A variety of illustrative assays that facilitate the determination of dose parameters for therapeutic cytokines are well known in the art and involve a variety of in vitro and in vivo methodologies (see, e.g. U.S. Pat. Nos. 6,575,169 and 6,041,788).

Certain embodiments of the invention include the step of determining the minimal amount of cytokine that will induce mRNA encoding SOCS 1 or SOCS 3 in the human cell. Preferably this step in the method based on previous pharmacokinetic studies of the cytokine (e.g. the range of a therapeutically effective dose) and is coupled with additional data such as the patient's sex, weight and age as well as the underlying causes of the condition or disease to be treated. Alternatively, prior to treatment, the individual themselves is tested in order to determine the optimal dose of therapeutic cytokine.

Typically, the minimal amount of cytokine that will induce mRNA encoding SOCS 1 or SOCS 3 in the human cell is determined in an assay that employs a Northern blot or polymerase chain reaction protocol. In an exemplary assay, an established pharmacokinetic and/or pharmacodynamic animal model such as a murine or simian model that is known to correlate with humans is used to titrate the minimal dose of cytokine necessary to induce mRNA encoding SOCS 1 or SOCS 3 in a particular cell type (e.g. a hepatocyte, a lymphocyte, a kidney cell, a pancreatic cell etc.). As is known in the art, in such assays Northern blot or polymerase chain reaction protocols can be used to examine the presence and/or levels of mRNA and/or duration of mRNA expression in cells taken from animals exposed to a series of doses of decreasing cytokine dilutions. In this way, the minimal amount of cytokine that will induce mRNA encoding SOCS 1 or SOCS 3 is empirically determinable. In certain embodiments of the invention, this concentration of cytokine can then be compared to the therapeutically effective range of cytokine concentrations so that an area overlap can be identified (i.e. a therapeutically effective dose that does not induce SOCS 1 or SOCS 3).

A related embodiment of the invention is a method of inhibiting the induction of mRNA encoding SOCS 1 (SEQ ID NO: 1) or SOCS 3 (SEQ ID NO: 3) polypeptide in a human cell exposed to a therapeutically effective amount of a cytokine capable of inducing the SOCS 1 or SOCS 3 mRNA, the method comprising the steps of determining the minimal amount of cytokine that will induce mRNA encoding SOCS 1 or SOCS 3 in the human cell; and then exposing the human cell to an therapeutically effective amount of a SOCS inducing cytokine that is less than the minimal amount of cytokine that will induce mRNA encoding SOCS 1 or SOCS 3 in the human cell, so that the induction of mRNA encoding SOCS 1 or SOCS 3 in the human cell is inhibited. Optionally, the amount of cytokine administered is the maximal dose of SOCS inducing cytokine that fails to induce mRNA encoding SOCS 1 (SEQ ID NO: 1) or SOCS 3 (SEQ ID NO: 3) (i.e. just under the minimal amount of cytokine that is required to induced SOCS).

A related embodiment of the invention is a method of inhibiting or controlling the induction of mRNA encoding SOCS 1 (SEQ ID NO: 1) or SOCS 3 (SEQ ID NO: 3) polypeptide in a human cell exposed to a therapeutically effective amount of a cytokine capable of inducing the sustained transcription of SOCS 1 or SOCS 3 mRNA (i.e. where the induction does not result in a mere transient increase in mRNA encoding SOCS 1 or SOCS 3). In particular, low doses of interferon induce transient increases in SOCS mRNA that return to baseline amounts after about 4 hours and remain low during the remainder of the low dosing period. In this context, the term "baseline" is used according to its art accepted meaning and refers, for example, to the typical amount of SOCS mRNA produced by a cell in a physiological environment that does not contain an exogenously added cytokine. In contrast, with higher concentrations of interferon, SOCS mRNA is sustained and continues to increase for 24 hours and remains elevated (e.g. levels that are 10%, 50%, 100% etc. above baseline) for the duration of the dosing period (see, e.g. Hu et al., Nature Immunology 3(9): 859-866 (2002)). In this context, this embodiment of the invention is tailored to avoid or control the sustained induction of SOCS mRNA. Methods for evaluating the sustained induction of SOCS mRNA can include for example assays designed to observe an increase in SOCS mRNA in cells 4 or 6 or 12 or 18 or 24 hours etc. after a dose of cytokine. This method comprises the steps of determining the minimal amount of cytokine necessary to produce a sustained induction mRNA encoding SOCS 1 or SOCS 3 in the human cell; and then exposing the human cell to an therapeutically effective amount of a SOCS inducing cytokine that is less than the minimal amount of cytokine necessary to produce a sustained induction of mRNA encoding SOCS 1 or SOCS 3 in the human cell, so that the induction of mRNA encoding SOCS 1 or SOCS 3 in the human cell is inhibited. In illustrative embodiments, the human cell is in a patient infected with a hepatitis virus, the cytokine is an interferon and the interferon is administered to the patient via continuous infusion. Preferably, this method results in at least a 90%, 95% or 99% decrease in viral levels (e.g. in the context of chronic infection with hepatitis B, hepatitis C, hepatitis D, hepatitis G etc.) in the patient.

Yet another embodiment of the invention is a method of controlling the biological activity of SOCS 1 (SEQ ID NO: 1) or SOCS 3 (SEQ ID NO: 3) in a human cell exposed to a therapeutically effective amount of a cytokine capable of inducing SOCS 1 or SOCS 3 biological activity, the method comprising the steps of determining the minimal amount of SOCS inducing cytokine that will induce SOCS 1 or SOCS 3 biological activity in the human cell; and then exposing the human cell to an therapeutically effective amount of a SOCS inducing cytokine that is less than the amount determined to be the minimal amount of SOCS inducing cytokine that will induce SOCS 1 or SOCS 3 biological activity in the human cell, so that the biological activity of SOCS 1 (SEQ ID NO: 1) or SOCS 3 (SEQ ID NO: 3) in a human cell is controlled. Optionally, the SOCS polypeptide is SOCS 1.

In the above described methods for controlling the biological activity of SOCS 1 (SEQ ID NO: 1) or SOCS 3 (SEQ ID NO: 3), the SOCS inducing cytokine used in the method is preferably an insulin (e.g. human insulin, porcine insulin, LISPRO insulin etc.). For example, insulin increases SOCS-3 mRNA expression in 3T3-L1 adipocytes and when expressed, SOCS-3 binds to phosphorylated Tyr(960) of the insulin receptor and prevents STAT 5 activation by insulin.

Moreover, it is known in the art that the insulin receptor substrate (IRS) proteins that are known act as important mediators of insulin action can be regulated, both positively and negatively, at the level of phosphorylation, and signalling through these proteins can be further modulated through the actions of SOCS proteins. See, e.g. Krebs et al., Sci STKE. 2003 Feb. 11; 2003(169):PE6; Johnstone et al., FEBS Lett. 546(1):32-6; Le et al., Mol Endocrinol. 2002 16(12):2764-79; Emanuelli et al., J Biol Chem. 2001; 276(51):47944-9; Monneyu et al., J Biol Chem. 2001; 276(28):25889-93; Peraldi et al., J Biol Chem. 2001; 276(27):24614-20; Sadowski et al., J Biol Chem. 2001; 276(23):20703-10; Kawazoe et al., J Exp Med. 2001; 193(2):263-9; Emanuelli et al., J Biol Chem. 2000 275(21):15985-91, which are incorporated herein by reference.

Alternatively, the SOCS inducing cytokine can be insulin-like growth factor-1, a growth hormone, prolactin, interleukin-2, interleukin-4, interleukin-6, interleukin-7, interleukin-10, interleukin-12, LIF, growth hormone, TPO, prolactin, stem cell factor, erythropoietin or tumor necrosis factor (see, e.g. Nicola et al., Experimental Hematology 28: 1105-1112 (2000); Starr et al., Nature, 387: 917 (1997); Song et al., J. Biol. Chem. 273: 35056 (1998); Sakamoto et al., Blood, 92: 1668 (1998); Trop et al., Blood, 97: 2269 (2001); Losman et al., J. Immunol. 162: 3770 (1999): Morita et al., P.N.A.S. 97: 5405 (2000); Sporri et al., Blood, 97: 221 (2001); Alexander et al., J. Leukocyte Biol. 66: 588 (1999); Yasukawa et al., Annu. Rev. immunol. 18: 143 (2000); Chen et al., Immunity, 132: 287 (2000); Gadina et al., Curr. Opin. Immunol. 13: 363 (2001). While these are illustrative cytokines for use the methods of the invention, the methods disclosed herein are applicable to all SOCS inducing cytokines, wherein the amount of cytokine necessary to induce SOCS 1 or SOCS 3 biological activity in the human cell is greater than the amount of cytokine necessary to effect at least one biological activity associated with the therapeutic aspect of the cytokine. Optionally, the human cell is in a patient and the cytokine is administered to the patient via continuous infusion.

Another method of the invention is a method of controlling the biological activity of SOCS 1 (SEQ ID NO: 1) or SOCS 3 (SEQ ID NO: 3) in a human cell exposed to a therapeutically effective amount of a cytokine capable of inducing SOCS 1 or SOCS 3 biological activity selected from the group consisting of human insulin, insulin-like growth factor-1, growth hormone, prolactin, interleukin-2, interleukin-4, interleukin-6, interleukin-7, interleukin-10, intetleukin-12, LIF, TPO, prolactin, stem cell factor, erythropoietin, tumor necrosis factor and interferon $\alpha$, $\beta$, or $\gamma$, the method comprising the steps of determining the minimal amount of SOCS inducing cytokine that will induce SOCS 1 or SOCS 3 biological activity in the human cell; and then exposing the human cell to an therapeutically effective amount of a SOCS inducing cytokine that is less than the amount determined to be the minimal amount of SOCS inducing cytokine that will induce SOCS 1 or SOCS 3 biological activity in the human cell, so that the biological activity of SOCS 1 (SEQ ID NO: 1) or SOCS 3 (SEQ ID NO: 3) in a human cell is controlled. Optionally, the invention is a method using only of the above enumerated cytokines.

In one embodiment, the human selected for treatment by the therapeutic methods of the invention is a nonresponder, that is has failed to respond to a previous treatment with a cytokine. Optionally, the cytokine has not been chemically modified (e.g. has not been chemically conjugated to a polyol such as polyethylene glycol). In illustrative embodiments of the invention the continuous administration is conducted subcutaneously. Typically, the cytokine is administered to the human by a continuous infusion pump.

In illustrative methods of the invention, the cytokine is used in combination with a second therapeutic agent. In an illustrative embodiments of the invention, the second therapeutic agent is 5-fluorouracil or ribavirin. Alternatively, the second therapeutic agent is an antibody. For example, HCV core protein is known to induce SOCS 3 expression and transcriptional activation of the SOCS 3 promoter (see, e.g. Bode et al., FASEB 490(17): 488-490 (2003). Consequently, in certain embodiments of the invention the interferon is used in combination an antibody capable of; (1) binding HCV core protein and; and (2) neutralizing its SOCS inducing activity.

Alternatively, the cytokine is used in combination with a polynucleotide that is complementary to an mRNA encoding SOCS 1 (SEQ ID NO: 1) or SOCS 3 (SEQ ID NO: 3). Specifically contemplated embodiments of the invention disclosed herein include ribozymes, and antisense molecules, as well as nucleic acid molecules based on an alternative backbone, or including alternative bases, whether derived from natural sources or synthesized, and include molecules capable of inhibiting the RNA or protein expression of SOCS 1 and/or SOCS 3. In addition, SOCS 1 and/or SOCS 3 polynucleotide that is complementary to an mRNA encoding SOCS 1 (SEQ ID NO: 1) or SOCS 3 (SEQ ID NO: 3) may be an siRNA (see, e.g. U.S. patent application Nos. 20030139363 and 20030153519). Antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the SOCS 1 and/or SOCS 3 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., SOCS 1 and/or SOCS 3. See for example, Jack Cohen, Oligodeoxynucleotides, Antisense Inhibitors of Gene Expression, CRC Press, 1989; and Synthesis 1:1-5 (1988). The SOCS antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693-4698 (1990); and Iyer, R. P. et al., J. Am. Chem. Soc. 112:1253-1254 (1990). SOCS 1 and/or SOCS 3 antisense oligonucleotides of the present invention include morpholino antisense oligonucleotides known in the art (see, e.g., Partridge et al., 1996, Antisense & Nucleic Acid Drug Development 6: 169-175).

As noted above, the sensitivity of cells to cytokines is regulated by the opposition of STAT1 and SOCS proteins that are expressed at different relative amounts, depending upon the intensity and/or duration of an activating stimulus (i.e. exposure to a cytokine). In this context, high expression of STAT1 will overcome or balance inhibition by SOCS proteins. Consequently, yet another embodiment of the invention is a method for modulating the relative levels of STAT1 and SOCS 1 and/or SOCS 3 in a cell, the method comprising exposing the cell to an amount of SOCS inducing cytokine that is capable of activating sustained STAT1 expression, wherein the amount of cytokine is selected so that it does not activate sustained feedback inhibition of cytokine signalling by SOCS 1 and/or SOCS 3, so that the relative levels of STAT1 and SOCS 1 and/or SOCS 3 in a cell are modulated.

In certain embodiments of the invention, the duration of the treatment is predetermined. In an illustrative embodiment, the duration of the treatment is at least 1, 2, 3, 4, 5, 6, 7, 8, 9, 10, 11 or 12 weeks. Alternatively, the duration of the treatment is based on a change in some factor associated with the progression of a cancer such as tumor size. Alternatively, the duration of the treatment is based on a change in some factor associated with viral infection such as the levels of detectable virus in the patient. For example, in certain embodiments of the invention, the method of treating the hepatitis viral infection results in a 50%, 90% or 95% decrease in hepatitis viral levels in the human. Alternatively, the duration of the treatment based upon an observation of a decrease in the levels of serum alanine aminotransferase (ALT) in the patient.

Other embodiments of the invention include methods for the preparation of a medication for the treatment of pathological conditions including viral infection by preparing a cytokine composition for administration to a mammal having the pathological condition, wherein the dose of interferon prepared is selected so as to be insufficient to activate feedback inhibition of cytokine activity by SOCS 1 (SEQ ID NO: 1) or SOCS 3 (SEQ ID NO: 3). Another embodiment is the use of an effective amount of a cytokine in the preparation of a medicament for the treatment of a cancer via a continuous infusion pump. A related method is the use of an effective amount of a cytokine in the preparation of a medicament for the treatment of chronic hepatitis infection via a continuous infusion pump. Optionally such medicaments include a second therapeutic agent. Such methods typically involve the steps of including an amount of cytokine sufficient to inhibit SOCS mRNA induction and the biological activity of SOCS polypeptides in vivo and an appropriate amount of a physiologically acceptable carrier. As is known in the art, optionally other agents can be included in these preparations.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container can hold a composition (e.g. cytokine or other therapeutic composition) which is effective for treating the condition (e.g. chronic hepatitis infection) and may have a sterile access port (for example the container may be an intravenous solution bag or a vial having a stopper pierceable by a hypodermic injection needle). The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The pharmaceutical compositions useful in the methods of the invention can be included in a container, pack, or dispenser together with instructions for administration. That result can be reduction and/or alleviation of the signs, symptoms, or causes of a disease or any other desired alteration of a biological system. For example, in a further embodiment of the invention, there are provided kits containing materials useful for treating pathological conditions with interferon. The article of manufacture comprises a container with a label. Suitable containers include, for example, bottles, vials, and test tubes. The containers may be formed from a variety of materials such as glass or plastic. The container holds a composition having an active agent which is effective for treating pathological conditions such as viral infection. The active agent in the composition is preferably interferon. The label on the container indicates that the composition is used for treating pathological conditions with interferon.

Throughout this application, various patents, patent applications, accession numbers (which, as is known in the art provide a reference of sequence and publication information), and other publications etc. are referenced. The disclosures of these publications etc. are hereby incorporated by reference herein in their entireties. The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention. However, the invention is only limited by the scope of the appended claims.

EXAMPLES

The following example is provided as an illustration of typical methods for examining the relationship between cytokine dose and the expression of SOCS 1 and/or SOCS 3. In this example, insulin is used as the illustrative cytokine.

Animals: A typical animal model used with insulin such as 6-week-old male C57/Black mice can be maintained under typical physiological conditions (e.g. fed ad libitum and/or fasted) before injection of a series of insulin doses (e.g. a limiting dilution series beginning at a maximal therapeutic dose of insulin followed by a series of progressively diluted doses) and a comparative control (e.g. phosphate-buffered saline). At some specified time period after insulin injection (e.g. 25 minutes, 1 hour, 4 hours, 24 hours etc.), the mice can be euthanized, and tissues can be removed and frozen in liquid nitrogen. Tissue lysates can be prepared for analysis of SOCS expression as is known in the art (see, e.g. Chen et al. (1997) *Proc. Natl. Acad. Sci. U.S.A.* 94, 2295-2300).

Reagents: A variety of insulins for use in these methods are commercially available. In addition, a variety of anti-SOCS 1 and SOCS 3 antibodies are known in the art. Alternatively, anti-SOCS 1 and SOCS 3 antibodies can be generated using well established hybridoma technologies. In addition, SOCS 1 and SOCS 3 mRNA may be measured in samples by, for example, a nested polymerase chain reaction assay that uses two sets of primers derived from a SOCS 1 and/or SOCS 3 gene sequence (see, e.g. Ausubel et al. eds., 1995, Current Protocols In Molecular Biology, Unit 18 (PCR Analysis)).

Cell Culture: For in vitro studies, typical cell culture models such as mouse skeletal muscle C2C12 myoblasts can be cultured in growth medium (e.g. Dulbecco's modified Eagle's medium containing 15% heat-inactivated fetal bovine serum, 0.5% chick embryo extract, 25 mM HEPES, and 0.2% gentamicin). For myoblast cultures, C2C12 cells can be grown to 80% of confluence on tissue culture dishes, can be washed with phosphate-buffered saline (PBS), and placed in placed in serum starvation media: Dulbecco's modified Eagle's medium supplemented with 0.2% bovine serum albumin and 25 mM HEPES. Such cell cultures can be kept under specific cell culture conditions (e.g. insulin absence) for some set period of time before exposing the cells to insulin or a control diluent (PBS).

TABLE 1A

SOCS-1 Polypeptide (see, e.g. NCBI protein database No. NP_003736; 015524; CAB92528)

MVAHNQVAADNAVSTAAEPRRRPEPSSSSSSSPAAPARPRPCPAVPAPAP  (SEQ ID NO: 1)

GDTHFRTFRSHADYRRITRASALLDACGFYWGPLSVHGAHERLRAEPVGT

FLVRDSRQRNCFFALSVKMASGPTSIRVHFQAGRFHLDGSRESFDCLFEL

LEHYVAAPRRMLGAPLRQRRVRPLQELCRQRIVATVGRENLARIPLNPVL

RDYLSSFPFQI

Immunopredpitation and Western Blotting In protocols that examine the presence of SOCS 1 and/or SOCS 3 proteins as well as those that examine SOCS 1 and/or SOCS 3 biological activities such as the phosphorylation of a second polypeptide, tissues and/or cell cultures can be used. In such protocols, tissue or cells can be lysed in radioimmune precipitation buffer under typical conditions. Lysates can be cleared of insoluble material by centrifugation. To evaluate the presence of SOCS 1 and/or SOCS 3 proteins, cleared lysates can be immunoprecipitated with anti-SOCS 1 or 3 antibodies and subjected to SDS-PAGE. Alternatively for Western blotting of whole cell lysates, cleared radioimmune precipitation buffer lysates containing equal protein can be boiled in SDS-PAGE sample buffer and subjected to SDS-PAGE. After electrophoretic transfer of proteins to nitrocellulose, the membranes can be blocked and then incubated with primary antibodies in the appropriate blocking buffer. The membranes can be can be processed, developed and exposed to film to analyze SOCS protein expression.

RNA Ex-traction and Northern Analysis and PCR: Northern and/or PCR protocols are typically used in procedures that examine the presence of SOCS 1 and/or SOCS 3 mRNA. For example, after the various sets of cells are exposed to the series of insulin dilutions, cells can be rinsed according to typical methodologies such as twice with ice-cold PBS, and total RNA can be extracted using typical methodologies. Fractionated or total RNA can be examined using a quantitative PCR analysis with SOCS 1 and/or SOCS 3 primer sets. Alternatively, total RNA can be fractionated by electrophoresis on agarose-formaldehyde gel, transferred to membrane and then fixed (e.g. by UV cross-linking). Such membranes can then be hybridized with $^{32}$P-radiolabeled antisense probe derived from polynucleotides encoding SOCS-1, or SOCS-3 (as well as a control probe such as actin). Membranes can be can washed at high stringency and then exposed to film to analyze SOCS mRNA expression.

Data Analysis. The assays noted above can be used to identify the concentration of insulin that is insufficient and/or sufficient to induce an mRNA encoding SOCS 1 (SEQ ID NO: 1) and/or SOCS 3 (SEQ ID NO: 3) and/or induce SOCS protein expression and/or induce SOCS protein activity. This data can then, for example, be compared with the known therapeutically effective range of insulin concentrations so that an area overlap can be identified for use in one or more therapeutic modalities (i.e. a therapeutically effective dose that does not induce SOCS 1 or SOCS 3).

Tables

TABLE 1B

SOCS-1 Polynucleotide (see, e.g. see, e.g. NCBI polynucleotide database No. NM_003745 or AF132440)

GGCAGCTGCACGGCTCCTGGCCCCGGAGCATGCGCGAGAGCCGCCCCGGA (SEQ ID NO: 2)
GCGCCCCGGAGCCCCCGCCGTCCCGCCCGCGGCGTCCCGCGCCCCGCCG
CCAGCGCACCCCCGGACGCTATGGCCCACCCCTCCGGCTGGCCCCTTCTG
TAGGATGGTAGCACACAACCAGGTGGCAGCCGACAATGCAGTCTCCACAG
CAGCAGAGCCCCGACGGCGGCCAGAACCTTCCTCCTCTTCCTCCTCCTCG
CCCGCGGCCCCCGCGCGCCCGCGGCCGTGCCCCGCGGTCCCGGCCCCGGC
CCCCGGCGACACGCACTTCCGCACATTCCGTTCGCACGCCGATTACCGGC
GCATCACGCGCGCCAGCGCGCTCCTGGACGCCTGCGGATTCTACTGGGGG
CCCCTGAGCGTGCACGGGGCGCACGAGCGGCTGCGCGCCGAGCCCGTGGG
CACCTTCCTGGTGCGCGACAGCCGCCAGCGGAACTGCTTTTTCGCCCTTA
GCGTGAAGATGGCCTCGGGACCCACGAGCATCCGCGTGCACTTTCAGGCC
GGCCGCTTTCACCTGGATGGCAGCCGCGAGAGCTTCGACTGCCTCTTCGA
GCTGCTGGAGCACTACGTGGCGGCGCCGCGCCGCATGCTGGGGGCCCCGC
TGCGCCAGCGCCGCGTGCGGCCGCTGCAGGAGCTGTGCCGCCAGCGCATC
GTGGCCACCGTGGGCCGCGAGAACCTGGCTCGCATCCCCCTCAACCCCGT
CCTCCGCGACTACCTGAGCTCCTTCCCCTTCCAGATTTGACCGGCAGCGC
CGCCGTGCACGCAGCATTAACTGGGATGCCGTGTTATTTTGTTATTACT
TGCCTGGAACCATGTGGGTACCCTCCCCGGCCTGGGTTGGAGGGAGCGGA
TGGGTGTAGGGGCGAGGCGCCTCCCGCCCTCGGCTGGAGACGAGGCCGCA
GACCCCTTCTCACCTCTTGAGGGGGTCCTCCCCCTCCTGGTGCTCCCTCT
GGGTCCCCCTGGTTGTTGTAGCAGCTTAACTGTATCTGGAGCCAGGACCT
GAACTCGCACCTCCTACCTCTTCATGTTTACATATACCCAGTATCTTTGC
ACAAACCAGGGGTTGGGGAGGGTCTCTGGCTTTATTTTCTGCTGTGCA
GAATCCTATTTTATATTTTTTAAAGTCAGTTTAGGTAATAAACTTTATTA
TGAAAGTTTTTTTTT

TABLE 1C

SOCS-3 Polypeptide (see, e.g. NCBI protein database No. NP_003946 or AAD42231)

MVTHSKFPAAGMSRPLDTSLRLKTFSSKSEYQLVVNAVRKLQESGFYWSA (SEQ ID NO: 3)
VTGGEANLLLSAEPAGTFLIRDSSDQRHFFTLSVKTQSGTKNLRIQCEGG
SFSLQSDPRSTQPVPRFDCVLKLVYHYMPPPGAPSFPSPPTEPSSEVPEQ
PSAQPLPGSPPRRAYYIYSGGEKIPLVLSRPLSSNVATLQHLCRKTVNGH
LDSYEKVTQLPGPIREFLDQYDAPL

TABLE 1D

SOCS-3 Polynucleotide (see, e.g. NCBI protein database No. NM_003955 or AF159854)

GCGCCTTCCTCTCCGCAGCCCCCGGGATGCGGTAGCGGCCGCTGTGCGG (SEQ ID NO: 4)
AGGCCGCGAAGCAGCTGCAGCCGCCGCCGCGCAGATCCACGCTGGCTCCG
TGCGCCATGGTCACCCACAGCAAGTTTCCCGCCGCCGGGATGAGCCGCCC
CCTGGACACCAGCCTGCGCCTCAAGACCTTCAGCTCCAAGAGCGAGTACC
AGCTGGTGGTGAACGCAGTGCGCAAGCTGCAGGAGAGCGGCTTCTACTGG
AGCGCAGTGACCGGCGGCGAGGCGAACCTGCTGCTCAGTGCCGAGCCCGC
CGGCACCTTTCTGATCCGCGACAGCTCGGACCAGCGCCACTTCTTCACGC
TCAGCGTCAAGACCCAGTCTGGGACCAAGAACCTGCGCATCCAGTGTGAG
GGGGGCAGCTTCTCTCTGCAGAGCGATCCCCGGAGCACGCAGCCCGTGCC
CCGCTTCGACTGCGTGCTCAAGCTGGTGTACCACTACATGCCGCCCCCTG
GAGCCCCCTCCTTCCCCTCGCCACCTACTGAACCCTCCTCCGAGGTGCCC
GAGCAGCCGTCTGCCCAGCCACTCCCTGGGAGTCCCCCCAGAAGAGCCTA
TTACATCTACTCCGGGGGCGAGAAGATCCCCCTGGTGTTGAGCCGGCCCC
TCTCCTCCAACGTGGCCACTCTTCAGCATCTCTGTCGGAAGACCGTCAAC
GGCCACTGGACTCCTATGAGAAAGTCACCCAGCTGCCGGGGCCCATTCG
GGAGTTCCTGGACCAGTACGATGCCCCGCTTTAAGGGGTAAAGGGCGCAA
AGGGCATGGGTCGGAGAGGGGACGCAGGCCCCTCTCCTCCGTGGCACAT

TABLE 1D

STAT1 Polypeptide (see, e.g. NCBI protein database No. NM_139266)

MSQWYELQQLDSKFLEQVHQLYDDSFPMEIRQYLAQWLEKQDWEHAANDV (SEQ ID NO: 5)
SFATIRFHDLLSQLDDQYSRFSLENNFLLQHNIRKSKRNLQDNFQEDPIQ
MSMIIYSCLKEERKILENAQRFNQAQSGNIQSTVMLDKQKELDSKVRNVK
DKVMCIEHEIKSLEDLQDEYDFKCKTLQNREHETNGVAKSDQKQEQLLLK
KMYLMLDNKRKEVVHKIIELLNVTELTQNALINDELVEWKRRQQSACIGG
PPNACLDQLQNWFTIVAESLQQVRQQLKKLEELEQKYTYEHDPITKNKQV
LWDRTFSLFQQLIQSSFVVERQPCMPTHPQRPLVLKTGVQFTVKLRLLVK
LQELNYNLKVKVLFDKDVNERNTVKGFRKFNILGTHTKVMNMEESTNGSL
AAEFRHLQLKEQKNAGTRTNEGPLIVTEELHSLSFETQLCQPGLVIDLET
TSLPVVVISNVSQLPSGWASILWYNMLVAEPRNLSFFLTPPCARWAQLSE
VLSWQFSSVTKRGLNVDQLNMLGEKLLGPNASPDGLIPWTRFCKENINDK
NFPFWLWIESILELIKKHLLPLWNDGCIMGFISKERERALLKDQQPGTFL
LRFSESSREGAITFTWVERSQNGGEPDFHAVEPYTKKELSAVTFPDIIRN
YKVMAAENIPENPLKYLYPNIDKDHAFGKYYSRPKEAPEPMELDGPKGTG
YIKTELISVSEV

The invention claimed is:

1. A method of avoiding the induction of mRNA encoding suppressor of cytokine signaling (SOCS) 1 (SEQ ID NO: 1) polypeptide in a human cell exposed to a therapeutically effective amount of gamma interferon capable of inducing the SOCS 1 mRNA, the method comprising the steps of:

(a) exposing the human cell to a series of gamma interferon dilutions to generate dose response data so as to identify the minimal amount of gamma interferon that will induce mRNA encoding SOCS 1 in the human cell; and (b) exposing the human cell to an therapeutically effective amount of a SOCS 1 inducing gamma interferon that is less than the minimal amount identified in step (a) so that the induction of mRNA encoding SOCS 1 in the human cell is avoided.

2. The method of claim 1, wherein the gamma interferon is combined with a pharmaceutically acceptable carrier.

3. The method of claim 1, wherein the gamma interferon is parenterally administered to a human.

4. The method of claim 1, wherein the human cell is in a patient and the gamma interferon is administered to the patient via continuous infusion.

5. The method of claim 4, wherein the gamma interferon is administered to the patient by a continuous infusion pump.

* * * * *

SEQUENCE LISTING

<160> NUMBER OF SEQ ID NOS: 5

<210> SEQ ID NO 1
<211> LENGTH: 211
<212> TYPE: PRT
<213> ORGANISM: Homo Sapiens

<400> SEQUENCE: 1

Met Val Ala His Asn Gln Val Ala Ala Asp Asn Ala Val Ser Thr Ala
 1               5                  10                  15

Ala Glu Pro Arg Arg Pro Glu Pro Ser Ser Ser Ser Ser Ser
            20                  25                  30

Pro Ala Ala Pro Ala Arg Pro Arg Pro Cys Pro Ala Val Pro Ala Pro
            35                  40                  45

Ala Pro Gly Asp Thr His Phe Arg Thr Phe Arg Ser His Ala Asp Tyr
        50                  55                  60

Arg Arg Ile Thr Arg Ala Ser Ala Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
            100                 105                 110

Phe Ala Leu Ser Val Lys Met Ala Ser Gly Pro Thr Ser Ile Arg Val
        115                 120                 125

His Phe Gln Ala Gly Arg Phe His Leu Asp Gly Ser Arg Glu Ser Phe
    130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
            180                 185                 190

Arg Ile Pro Leu Asn Pro Val Leu Arg Asp Tyr Leu Ser Ser Phe Pro
        195                 200                 205

Phe Gln Ile
    210

<210> SEQ ID NO 2
<211> LENGTH: 1216
<212> TYPE: DNA
<213> ORGANISM: Homo Sapiens

<400> SEQUENCE: 2
ggcagctgca cggctcctgg ccccggagca tgcgcgagag ccgccccgga gcgccccgga      60 gcccccgcc gtcccgcccg cggcgtcccg cgcccgccg ccagcgcacc cccggacgct      120
atggcccacc cctccggctg cccccttctg taggatggta gcacacaacc aggtggcagc      180
cgacaatgca gtctccacag cagcagagcc ccgacggcgg ccagaacctt cctcctcttc      240
ctcctcctcg cccgcggccc ccgcgcgccc gcggccgtgc cccgcggtcc cggccccggc      300
ccccggcgac acgcacttcc gcacattccg ttcgcacgcc gattaccggc gcatcacgcg      360
cgccagcgcg ctcctggacg cctgcggatt ctactggggg cccctgagcg tgcacggggc      420
gcacgagcgg ctgcgcgccg agcccgtggg caccttcctg gtgcgcgaca gccgccagcg      480
gaactgcttt ttcgccctta gcgtgaagat ggcctcggga cccacgagca tccgcgtgca      540

-continued

| | | | | |
|---|---|---|---|---|
| ctttcaggcc | ggccgctttc | acctggatgg | cagccgcgag | agcttcgact gcctcttcga | 600 |
| gctgctggag | cactacgtgg | cggcgccgcg | ccgcatgctg | ggggccccgc tgcgccagcg | 660 |
| ccgcgtgcgg | ccgctgcagg | agctgtgccg | ccagcgcatc | gtggccaccg tgggccgcga | 720 |
| gaacctggct | cgcatccccc | tcaacccgt | cctccgcgac | tacctgagct ccttccccctt | 780 |
| ccagatttga | ccggcagcgc | ccgccgtgca | cgcagcatta | actgggatgc cgtgttattt | 840 |
| tgttattact | tgcctggaac | catgtgggta | ccctccccgg | cctgggttgg agggagcgga | 900 |
| tgggtgtagg | ggcgaggcgc | ctcccgccct | cggctggaga | cgaggccgca gacccttct | 960 |
| cacctcttga | ggggtcctc | cccctcctgg | tgctccctct | gggtccccct ggttgttgta | 1020 |
| gcagcttaac | tgtatctgga | gccaggacct | gaactcgcac | ctcctacctc ttcatgttta | 1080 |
| catataccca | gtatctttgc | acaaaccagg | ggttggggga | gggtctctgg ctttattttt | 1140 |
| ctgctgtgca | gaatcctatt | ttatattttt | taaagtcagt | ttaggtaata aactttatta | 1200 |
| tgaaagtttt | tttttt | | | | 1216 |

<210> SEQ ID NO 3
<211> LENGTH: 225
<212> TYPE: PRT
<213> ORGANISM: Homo Sapiens

<400> SEQUENCE: 3

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His Tyr Met
        115                 120                 125

Pro Pro Pro Gly Ala Pro Ser Phe Pro Ser Pro Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225
```

<210> SEQ ID NO 4
<211> LENGTH: 850

<212> TYPE: DNA
<213> ORGANISM: Homo Sapiens

<400> SEQUENCE: 4

```
gcgccttcct ctccgcagcc ccccgggatg cggtagcggc cgctgtgcgg aggccgcgaa      60
gcagctgcag ccgccgccgc gcagatccac gctggctccg tgcgccatgg tcacccacag     120
caagtttccc gccgccggga tgagccgccc cctggacacc agcctgcgcc tcaagacctt     180
cagctccaag agcgagtacc agctggtggt gaacgcagtg cgcaagctgc aggagagcgg     240
cttctactgg agcgcagtga ccggcggcga ggcgaacctg ctgctcagtg ccgagcccgc     300
cggcaccttt ctgatccgcg acagctcgga ccagcgccac ttcttcacgc tcagcgtcaa     360
gacccagtct gggaccaaga acctgcgcat ccagtgtgag ggggcagct tctctctgca      420
gagcgatccc cggagcacgc agcccgtgcc ccgcttcgac tgcgtgctca agctggtgta     480
ccactacatg ccgccccctg agccccctc cttcccctcg ccacctactg aaccctcctc      540
cgaggtgccc gagcagccgt ctgcccagcc actccctggg agtccccca gaagagccta      600
ttacatctac tccgggggcg agaagatccc cctggtgttg agccggcccc tctcctccaa     660
cgtggccact cttcagcatc tctgtcggaa gaccgtcaac ggccacctgg actcctatga     720
gaaagtcacc cagctgccgg ggcccattcg ggagttcctg gaccagtacg atgccccgct     780
ttaagggta aagggcgcaa agggcatggg tcgggagagg ggacgcaggc ccctctcctc      840
cgtggcacat                                                            850
```

<210> SEQ ID NO 5
<211> LENGTH: 712
<212> TYPE: PRT
<213> ORGANISM: Homo Sapiens

<400> SEQUENCE: 5

```
Met Ser Gln Trp Tyr Glu Leu Gln Gln Leu Asp Ser Lys Phe Leu Glu
  1               5                  10                  15

Gln Val His Gln Leu Tyr Asp Asp Ser Phe Pro Met Glu Ile Arg Gln
                 20                  25                  30

Tyr Leu Ala Gln Trp Leu Glu Lys Gln Asp Trp Glu His Ala Ala Asn
             35                  40                  45

Asp Val Ser Phe Ala Thr Ile Arg Phe His Asp Leu Leu Ser Gln Leu
         50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
                100                 105                 110

Arg Lys Ile Leu Glu Asn Ala Gln Arg Phe Asn Gln Ala Gln Ser Gly
            115                 120                 125

Asn Ile Gln Ser Thr Val Met Leu Asp Lys Gln Lys Glu Leu Asp Ser
        130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
```

-continued

```
            195                 200                 205
Lys Arg Lys Glu Val Val His Lys Ile Ile Glu Leu Leu Asn Val Thr
    210                 215                 220
Glu Leu Thr Gln Asn Ala Leu Ile Asn Asp Glu Leu Val Glu Trp Lys
225                 230                 235                 240
Arg Arg Gln Gln Ser Ala Cys Ile Gly Gly Pro Pro Asn Ala Cys Leu
                245                 250                 255
Asp Gln Leu Gln Asn Trp Phe Thr Ile Val Ala Glu Ser Leu Gln Gln
            260                 265                 270
Val Arg Gln Gln Leu Lys Lys Leu Glu Glu Leu Glu Gln Lys Tyr Thr
        275                 280                 285
Tyr Glu His Asp Pro Ile Thr Lys Asn Lys Gln Val Leu Trp Asp Arg
    290                 295                 300
Thr Phe Ser Leu Phe Gln Gln Leu Ile Gln Ser Ser Phe Val Val Glu
305                 310                 315                 320
Arg Gln Pro Cys Met Pro Thr His Pro Gln Arg Pro Leu Val Leu Lys
                325                 330                 335
Thr Gly Val Gln Phe Thr Val Lys Leu Arg Leu Leu Val Lys Leu Gln
            340                 345                 350
Glu Leu Asn Tyr Asn Leu Lys Val Lys Val Leu Phe Asp Lys Asp Val
        355                 360                 365
Asn Glu Arg Asn Thr Val Lys Gly Phe Arg Lys Phe Asn Ile Leu Gly
    370                 375                 380
Thr His Thr Lys Val Met Asn Met Glu Glu Ser Thr Asn Gly Ser Leu
385                 390                 395                 400
Ala Ala Glu Phe Arg His Leu Gln Leu Lys Glu Gln Lys Asn Ala Gly
                405                 410                 415
Thr Arg Thr Asn Glu Gly Pro Leu Ile Val Thr Glu Glu Leu His Ser
            420                 425                 430
Leu Ser Phe Glu Thr Gln Leu Cys Gln Pro Gly Leu Val Ile Asp Leu
        435                 440                 445
Glu Thr Thr Ser Leu Pro Val Val Val Ile Ser Asn Val Ser Gln Leu
    450                 455                 460
Pro Ser Gly Trp Ala Ser Ile Leu Trp Tyr Asn Met Leu Val Ala Glu
465                 470                 475                 480
Pro Arg Asn Leu Ser Phe Phe Leu Thr Pro Pro Cys Ala Arg Trp Ala
                485                 490                 495
Gln Leu Ser Glu Val Leu Ser Trp Gln Phe Ser Ser Val Thr Lys Arg
            500                 505                 510
Gly Leu Asn Val Asp Gln Leu Asn Met Leu Gly Glu Lys Leu Leu Gly
        515                 520                 525
Pro Asn Ala Ser Pro Asp Gly Leu Ile Pro Trp Thr Arg Phe Cys Lys
    530                 535                 540
Glu Asn Ile Asn Asp Lys Asn Phe Pro Phe Trp Leu Trp Ile Glu Ser
545                 550                 555                 560
Ile Leu Glu Leu Ile Lys Lys His Leu Leu Pro Leu Trp Asn Asp Gly
                565                 570                 575
Cys Ile Met Gly Phe Ile Ser Lys Glu Arg Glu Arg Ala Leu Leu Lys
            580                 585                 590
Asp Gln Gln Pro Gly Thr Phe Leu Leu Arg Phe Ser Glu Ser Ser Arg
        595                 600                 605
Glu Gly Ala Ile Thr Phe Thr Trp Val Glu Arg Ser Gln Asn Gly Gly
    610                 615                 620
```

-continued

```
Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
    690                 695                 700

Glu Leu Ile Ser Val Ser Glu Val
705                 710
```